(12) United States Patent
McCormick

(10) Patent No.: US 6,855,750 B2
(45) Date of Patent: Feb. 15, 2005

(54) METHOD AND APPARATUS FOR CREATING MOLDS

(76) Inventor: Edmund J. McCormick, 18 Bank St., Summit, NJ (US) 07901

( * ) Notice: Subject to any disclaimer, the term of this patent is extended or adjusted under 35 U.S.C. 154(b) by 260 days.

(21) Appl. No.: 10/245,086

(22) Filed: Sep. 17, 2002

(65) Prior Publication Data

US 2003/0020209 A1 Jan. 30, 2003

(51) Int. Cl.⁷ .................................................. A61K 6/10
(52) U.S. Cl. ........................ 523/109; 106/35; 264/222
(58) Field of Search .............................. 264/219, 222; 425/175, 2; 106/35; 523/109

(56) References Cited

U.S. PATENT DOCUMENTS 4,735,752 A * 4/1988 Negethon, Jr. ............... 264/19
5,096,754 A * 3/1992 Hammer et al. ........... 428/34.8
5,143,584 A * 9/1992 Hammer et al. ............. 162/175

FOREIGN PATENT DOCUMENTS

| DE | 37 42 450 | * 6/1989 |
| WO | WO 97/39170 | * 10/1997 |

\* cited by examiner

*Primary Examiner*—Allan R. Kuhns
(74) *Attorney, Agent, or Firm*—Walter J. Tencza, Jr.

(57) ABSTRACT

Minute fibers are added to an alginate to form a fiber-alginate mixture or compound. The minute fibers may be man made such as nylon or may be natural such as hemp. The fiber-alginate mixture or compound is used in forming a mold, which may be used in casting directly from the human body. The addition of the minute fibers to the alginate creates enormous tear strength, which is far better than the tear strength of the alginate alone. The alginate and the fibers should be mixed in an alginate to fiber ratio by weight of about twenty-four to one for a natural fiber and a ratio of four to one for a man made fiber.

15 Claims, 2 Drawing Sheets

METHOD AND APPARATUS FOR CREATING MOLDS

FIELD OF THE INVENTION

This invention relates to improved methods and apparatus concerning creating molds particularly molds directed towards obtaining a mold or casting directly from the human body.

BACKGROUND OF THE INVENTION

Typically in the prior art materials used for creating molds or casting directly from the human body are comprised of alginate. For example, alginate has been used since at least 1942 by dentists to take dental Impressions. Various standard alginate products are well known. Alginate products, in the prior art generally lack tear strength when the alginate products set as these products have the consistency of a hard boiled egg with the egg's shell removed.

SUMMARY OF THE INVENTION

In at least one embodiment of the present invention, minute fibers (such as about 3,125 microns in length +/−15% and 22 to 24 microns in diameter) are added to an alginate. The minute fibers may be made of natural material such as hemp or similar materials or man made (inorganic) material such as nylon, or similar materials. The particular type of fiber material does not necessarily matter, as it is the fiber itself bound to the hardened alginate that creates the strength much like steel rods added to concrete. The addition of the minute fibers to the alginate creates enormous tear strength greatly enhancing product performance.

The alginate and the fibers should be mixed together in proportions ranging from four to twenty percent depending upon strength required and type of fiber. A smoother fiber such as nylon requires a higher concentration of fiber, whereas a rough-textured fiber such as natural hemp requires a lower concentration of fiber. For a nylon-alginate mixture, for example, twenty ounces of nylon plus eighty ounces of alginate would be used to form one hundred ounces of a nylon alginate mixture. In this example the ratio of the weight of the alginate to the weight of the nylon fiber is 80/20 or 4/1. For a hemp-alginate mixture, for example, four ounces of hemp plus ninety-six ounces of alginate would be used to form one hundred ounces of a hemp-alginate mixture. In this example the ratio weight of the alginate to the weight of the hemp fiber is 96/4 or 24/1.

DETAILED DESCRIPTION OF THE DRAWINGS

Figure 1:
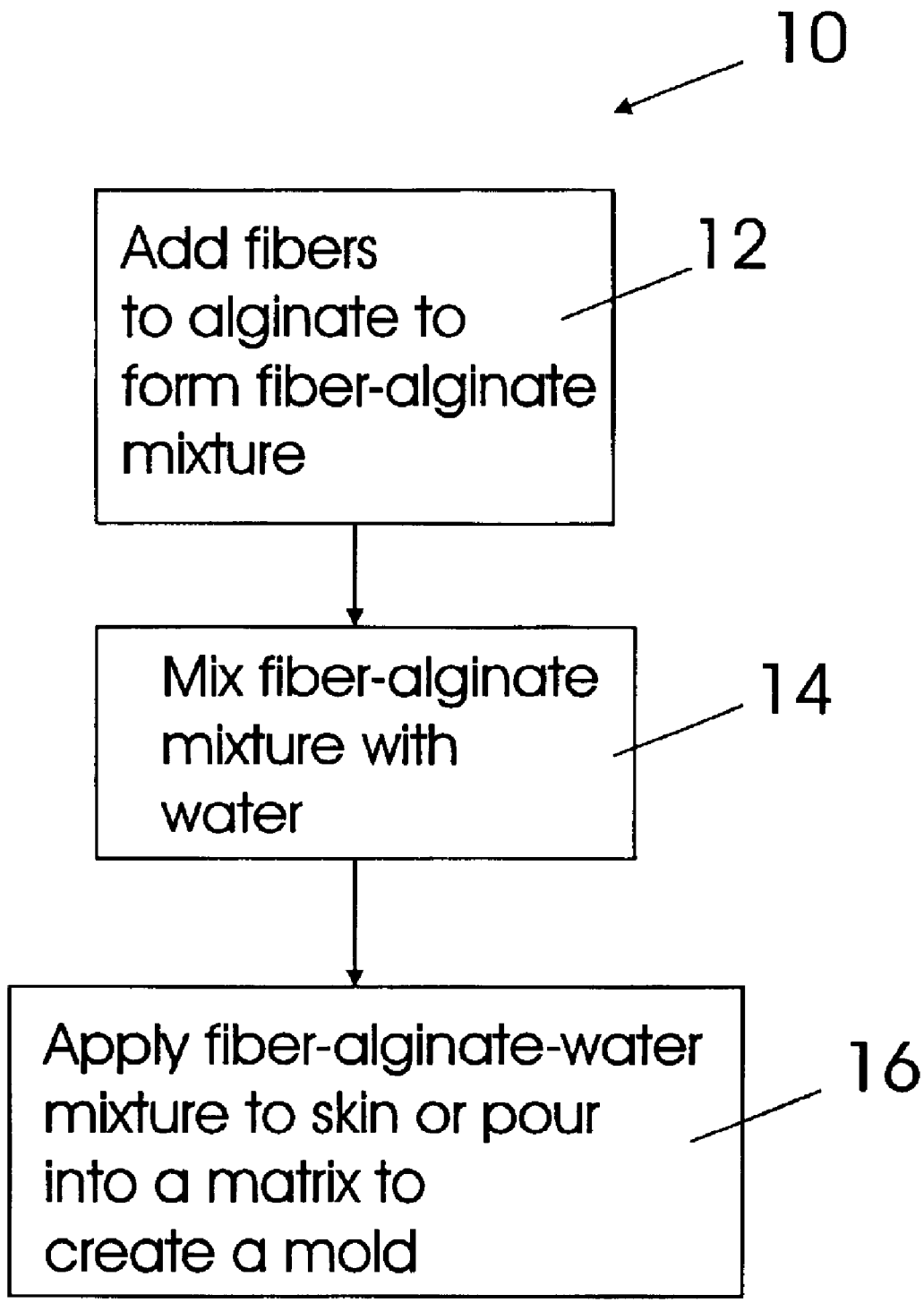
FIG. 1 shows a flow chart of a method in accordance with an embodiment of the present invention.

FIG. 1 shows a flow chart 10 of a method in accordance with an embodiment of the present invention. At step 12 of the flow chart 10 fibers are mixed with or added to an alginate to form a fiber-alginate mixture. Four to twenty percent fiber is typically blended with an alginate powder in a commercial blender such as a ribbon mixer. For example, four ounces of hemp fiber may be blended with ninety-six ounces of alginate powder to form one hundred ounces of hemp-alginate mixture.

The alginate can be any known alginate used in forming molds particularly molds for casting directly from the human body. At step 14 the alginate-fiber mixture is mixed with water and then formed into a mold. The alginate and fiber mixture is in powder form. It is activated by adding water in a proportion of approximately five ounces of alginate-fiber to one pound of water. Mixing is done with a wire whisk or a mixer that will not introduce air such as a Jiffy Mixer (trademarked) which is a long-time used mixer well known and popular in the industry) until the product (fiber-alginate-water mixture) reaches the consistency of thick yogurt. It is then ready for application at step 16 either in a matrix or applied directly to the skin.

Figure 2A:
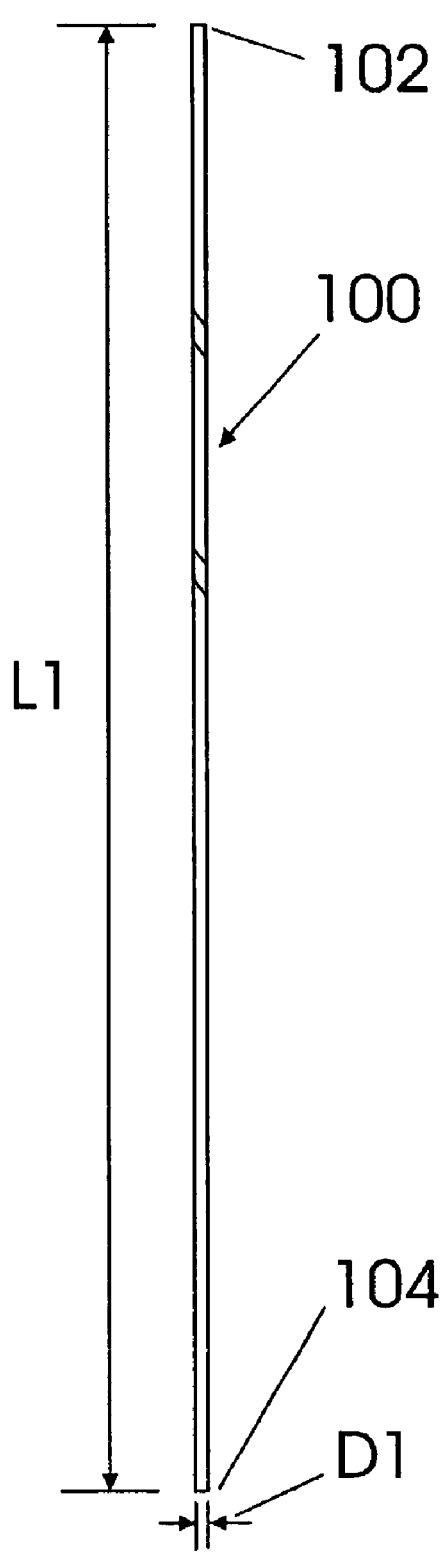
FIG. 2A shows a top view of a fiber for use in accordance with an embodiment of the present invention.
Figure 2B:
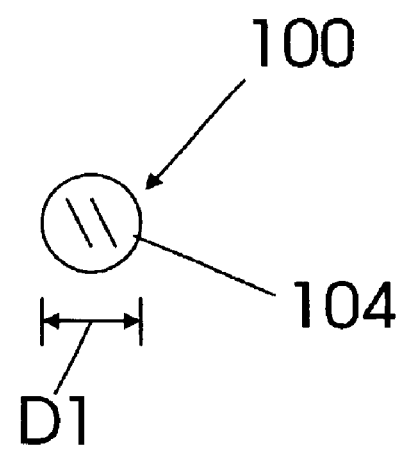
FIG. 2B shows a side view of the fiber of FIG. 2A.

FIG. 2A shows a top view of a fiber 100 for use in accordance with an embodiment of the present invention. The bottom view of fiber 100 not shown may be substantially identical to the top view. The fiber 100 may be shaped in the form of a solid elongated tube. The fiber 100 has a length L1, which may be one eighth of an inch (i.e. about 3,125 microns or micrometers). FIG. 2B shows a side view of the fiber 100 of FIG. 2A. The fiber 100 may be a natural or organic fiber, such as hemp, or a man made or inorganic fiber, such as nylon. The fiber 100 has an end or side 102 and an end or side 104. The ends or sides 102 and 104 have a diameter of D1, which may be twenty-two to twenty-four microns (micrometers). The ends 102 and 104 may be substantially identical.

The length, L1, of the fiber 100 typically may vary plus or minus fifteen percent from 3,125 (⅛ of an inch) microns for the purpose of the present invention. A typical range for the length L1 would thus be 3125 microns (⅛ or 0.125 of an inch)+/−468.75 microns (0.01875 of an inch). The inventor has determined, based on testing that this range for length L1 and the range of twenty-two to twenty-four microns for D1 creates a tear resistant material for the purposes of the present invention.

Although the invention has been described by reference to particular illustrative embodiments thereof, many changes and modifications of the invention may become apparent to those skilled in the art without departing from the spirit and scope of the invention. It is therefore intended to include within this patent all such changes and modifications as may reasonably and properly be included within the scope of the present invention's contribution to the art.

I claim:

1. An apparatus comprising:

a plurality of fibers; and an alginate;

wherein the plurality of fibers is mixed with the alginate to form an alginate-fiber mixture;

and wherein each of the plurality of fibers is substantially tube shaped and is about one eighth of an inch long and each of the plurality of fibers is about twenty-two to twenty-four micrometers in diameter.

2. The apparatus of claim 1 wherein a first weight of the plurality of fibers is mixed with a second weight of the alginate;

wherein the ratio of the second weight to the first weight is in the range of about twenty-four to one and tour to one.

3. The apparatus of claim 1 wherein each of the plurality of fibers is a man made fiber.

4. The apparatus of claim 3 wherein each of the plurality of fibers is comprised of nylon.

5. The apparatus of claim 1 wherein
each of the plurality of fibers is a natural fiber.
6. The apparatus of claim 5 wherein
each of the plurality of fibers is comprised of hemp.
7. An apparatus comprising:
a plurality of fibers; and
an alginate;
wherein the plurality of fibers is mixed with the alginate to form an alginate-fiber mixture;
wherein each of the plurality of fibers is a man made fiber;
wherein a first weight of the plurality of fibers is mixed with a second weight of the alginate; and
wherein the ratio of the second weight to the first weight is about seventeen to three.
8. An apparatus comprising:
a plurality of fibers; and
an alginate;
wherein the plurality of fibers is mixed with the alginate to form an alginate-fiber mixture;
wherein each of the plurality of fibers is a natural fiber; wherein
a first weight of the plurality of fibers is mixed with a second weight of the alginate; and
wherein the ratio of the second weight to the first weight is about twenty-four to one.
9. A method comprising the step of:
mixing a plurality of fibers with an alginate to form art alginate-fiber mixture; and
wherein each of the plurality of fibers is substantially tube shaped and is about one eighth of an inch long and each of the plurality of fibers is about twenty-four to twenty-four micrometers in diameter.
10. The method of claim 9 wherein
each of the plurality of fibers is a natural fiber.
11. The method of claim 10 wherein
each of the plurality of fibers is comprised of hemp.
12. The method of claim 9 wherein
each of the plurality of fibers is a man made fiber.
13. The method of claim 12 wherein
each of the plurality of fibers is comprised of nylon.
14. A method comprising the step of:
mixing a plurality of fibers with an alginate to form an alginate-fiber mixture;
wherein each of the plurality of fibers is a natural fiber;
wherein a first weight of the plurality of fibers is mixed with a second weight of the alginate; and
wherein the ratio of the second weight to the first weight is about twenty-four to one.
15. A method comprising the step of:
mixing plurality of fibers with an alginate to form an alginate-fiber mixture;
wherein each of the plurality of fibers is a man made fiber;
wherein a first weight of the plurality of fibers is mixed with a second weight of the alginate; and
wherein the ratio of the second weight to the first weight is about four to one.

* * * * *

UNITED STATES PATENT AND TRADEMARK OFFICE
CERTIFICATE OF CORRECTION

PATENT NO. : 6,855,750 B2
DATED : February 15, 2005
INVENTOR(S) : McCormick

It is certified that error appears in the above-identified patent and that said Letters Patent is hereby corrected as shown below:

Column 2,
Line 61, "tour" should be -- four --;

Column 4,
Line 1, "twenty-four" should be -- twenty-two --; and
Line 20, "mixing plurality" should be -- mixing a plurality --.

Signed and Sealed this

Seventh Day of June, 2005

JON W. DUDAS
*Director of the United States Patent and Trademark Office*